United States Patent [19]

Smith

[11] Patent Number: 5,611,799

[45] Date of Patent: Mar. 18, 1997

[54] OCULAR REPAIR METHOD

[76] Inventor: Albert C. Smith, P.O. Box 782, Los Altos, Calif. 94022

[21] Appl. No.: 566,678

[22] Filed: Dec. 4, 1995

Related U.S. Application Data

[62] Division of Ser. No. 259,482, Jun. 14, 1994.

[51] Int. Cl.⁶ ................................... A61B 17/00
[52] U.S. Cl. ............................. 606/32; 606/41; 607/116; 607/148
[58] Field of Search .................................. 607/116, 115, 607/141, 148, 51; 606/41, 32, 34; 128/639, 642; 361/232

[56] References Cited

U.S. PATENT DOCUMENTS 3,750,672 8/1973 Berckham ............................... 607/115
4,915,110 4/1990 Kitov ......................................... 607/51

Primary Examiner—Lee S. Cohen
Attorney, Agent, or Firm—Albert C. Smith

[57] ABSTRACT

Apparatus and method for surgical repair of a detached retina includes an array of insulated electrodes that can be positioned adjacent the rear of an eye near the detachment site for selective excitation of pairs of the electrodes to selectively develop electrostatic attractive force on the retina that is detached from the rear of the eye. The array of electrodes may be selectively deployed and retrieved from the distal end of the cannula which can be positioned near the detachment site to facilitate orientation and control of the electrostatic force. Plural electrodes in multiple sets may be selectively activated in order to reposition of the electrostatic force without substantially altering the position of the array near the rear of the eye. A controllable power supply may include manual and foot-actuated controls for switching multiple sets of electrodes and altering the magnitude of the electrostatic force developed at the operational site. Cryopexy or photocoagulation or diathermy techniques may be utilized to scarify the attachment of the retina to the rear wall of the eye once the detached retina is repositioned against the rear wall of the eye by the attractive electrostatic force exerted on the retina.

7 Claims, 4 Drawing Sheets

OCULAR REPAIR METHOD

This is a divisional of copending application Ser. No. 08/259,482 filed on Jun. 14, 1994.

FIELD OF THE INVENTION

This invention relates to eye surgery and more particularly to the techniques for repairing detachment of the retina from the back wall of the eye using minimally invasive apparatus for repositioning the retina against the back wall of the eye in condition for reattachment via cryosurgical techniques or laser photocoagulation techniques.

BACKGROUND OF THE INVENTION

Detachment of the retina from the rear wall of the eye as a result of injury or aging or disease is a common cause of blindness that can be corrected with varying degrees of success using contemporary surgical techniques. For example, small tears or holes that initially appear in the retina may be treated by laser photocoagulation techniques that rely upon forming small burns and scarring sites on the retina using focused laser light on target sites around the holes and tears. Alternatively, cryopexy or freezing local sites on the back of the eyeball causes similar scarring sites that promote scarified adhesion of the retina to the back wall of the eye. However, where the retina has pulled away from the back of the eye, it must be repositioned against the back wall of the eye to squeeze out fluid and reposition the retina in order for a scarified adhesion to successfully reattach the retina. A gas bubble may be injected into the eye to urge the retina against the back wall of the eye while the scarring takes place. In more complicated detachments of the retina, a silicone rubber pad or band may have to be installed against the back side of the eye in order to indent the back wall and thereby form contact with the retina at locations that can then support scarified adhesions using laser photocoagulation focused at such sites. These techniques tend to be effective but disabling to the patient who may have to remain in fixed head positions as much as possible for several days before and after the surgery to promote proper repositioning of the retina while scarified adhesions form to retain the retina in position against the back wall of the eye. Also, the injection of a gas bubble into the eye is effective substantially only for use with retinal detachments that occur in the upper regions of the eye since the gas bubble can be conveniently positioned only near the upper regions in reliance upon its buoyancy in the vitreous fluid in the eye, and in reliance upon the patient being able to position the head to assure orientation of the gas bubble adjacent the detached portion of the retina.

SUMMARY OF THE INVENTION

In accordance with the present invention, an improved system, method and apparatus are provided for selectively positioning the retina against the back wall of the eyeball to promote scarified reattachment via cryopexy or diathermy or laser photocoagulation. The present invention relies upon the properties of the retina as a poorly conductive layer of tissue to which a controlled positioning force can be applied from the back side of the eye in response to an applied electric field that is oriented about the region of the detached portion of the retina. In this way, even detachments of the retina occurring in the lower regions of the eye where the injection of a gas bubble is not a practical consideration can be positioned selectively by application of an electric field in controlled strength, orientation, and duration for proper placement and subsequent reattachment by scarification according to conventional means. The force that is applied to the retinal layer of cells is attributable to the physical effect known as Coulomb's Inverse Square Law by which an insulating or semiconductive layer tends to be attracted by an electric field. Specifically, the force between two electrostatically charged bodies is proportional to the product of the magnitude of charges on the bodies and inversely proportional to the square of the distance between them according to the formula:

$$F=KQ_1Q_2/r^2 \qquad (\text{Eq. 1})$$

where F is the resultant electrostatic force between the charged bodies, $Q_1$ and $Q_2$ are the magnitudes of the charges on the surfaces of the two bodies, K is a factor indicative of the ratio of the dielectric constant of the medium separating the charged bodies to the dielectric constant for free space, and r is the distance between the charged bodies. In order to establish an attracting force between an insulating (or semiconductor) layer of material and an associated force-generating apparatus, a concentration of electrical charges of one polarity is required in the apparatus and a concentration of charges of opposite charges is required in the layer of insulating or (semiconductor) material. Perhaps two primary sources of electrical charges can be attracted in a retinal layer, including free charged particles that are believed to be available within the environment of the retinal layer, and the bound charge concentration associated with the polar characteristics of the material of the retinal layer. By positioning a structure of electrical conductors behind the eye at locations selectively disposed to attract the poorly-conductive retinal layer into place against the back wall of the eye, and by selectively controlling the strength and orientation of the resulting electric fields, the retinal layer can be effectively repositioned against the back of the eye for scarified reattachment. The structure of electrical conductors may be removed from behind the eye following repositioning of the detached portion of the retinal layer against the back wall of the eye to facilitate the scarified attachments form permanent adhesions to the back wall of the eye.

DESCRIPTION OF THE PREFERRED EMBODIMENT

Figure 1:
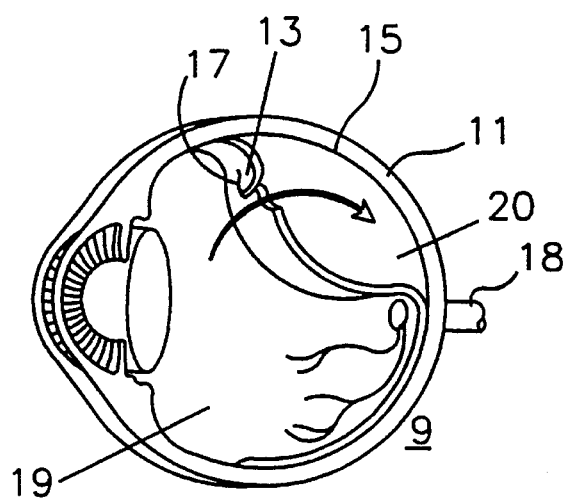
FIG. 1 is a pictorial, partially cut-away illustration of an eye with retinal detachment.

Referring now to FIG. 1, there is shown an eye 9 including an outer wall of scleral tissue 11 with the retinal layer 13 separated or detached from the back wall 15 of the eye. An intermediate layer, called the uvea, contains many of the blood vessels that nourish the eye. All of these layers of tissue exhibit poor electrical conductivity as dominantly organic materials. As such condition of retinal detachment occurs, due to injury or aging or disease, the retinal layer 13 may also tear 17, causing bleeding into the vitreous material 19 that fills the rear portion of the eye. If this condition is left untreated, the vitreous material 19 pervades the space 20 between the back wall 15 and the retina 13 and promotes further detachment and possible tearing of the retina 13 with resulting partial or complete blindness. The vitreous material 19 is an organic, gelatinous material which is not vascularized and which also exhibits poor electrical conductivity.

Figure 2:
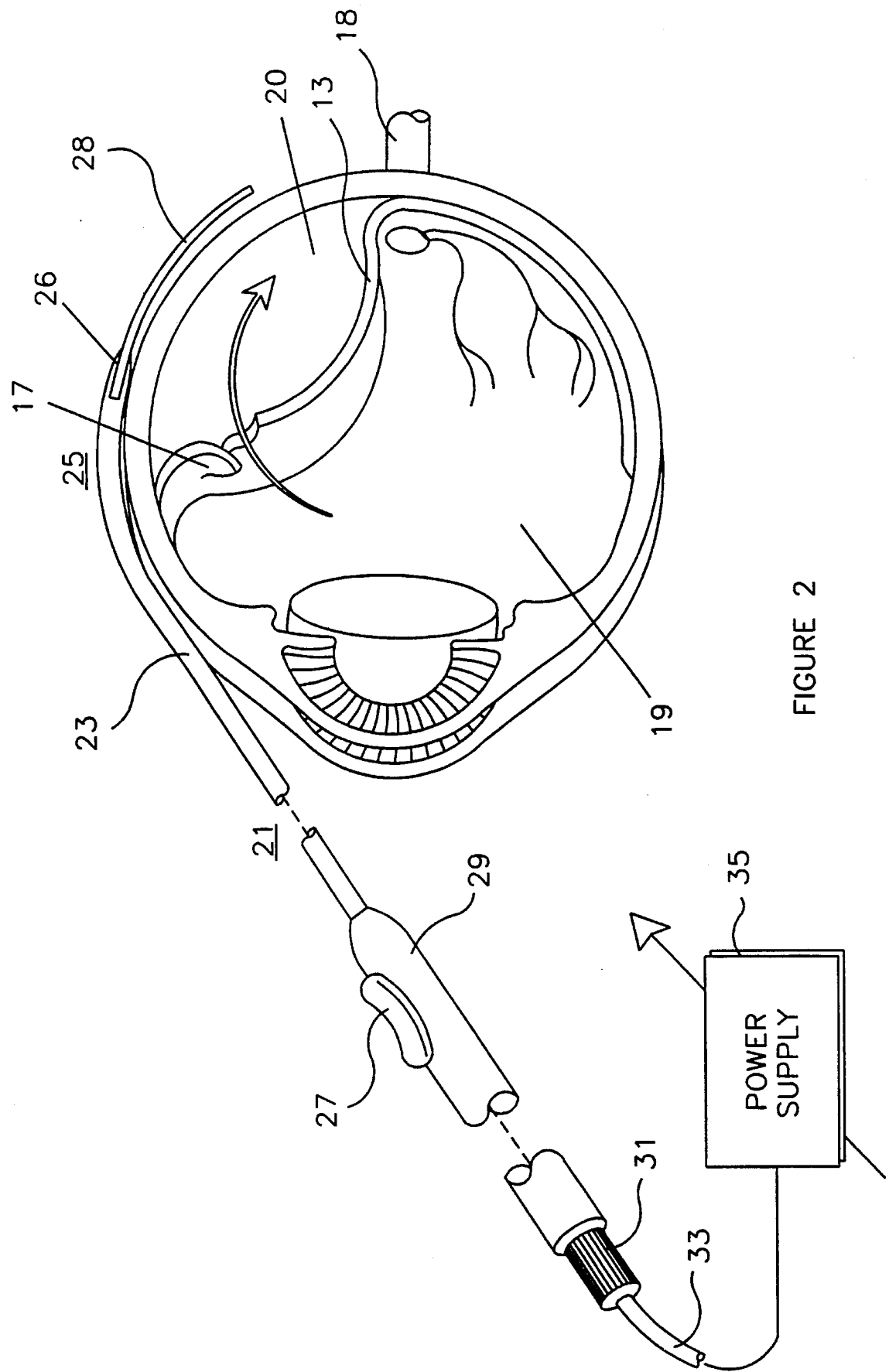
FIG. 2 is a pictorial, partially cut-away illustration of the eye according to FIG. 1 with the apparatus of the present invention inserted behind the eye adjacent the detachment of the retina for imposing a repositioning force thereon.

In accordance with the present invention, an electrode structure 21 is inserted into position behind the eye in the region away from the optic nerve 18 and adjacent the retinal detachment, as illustrated in FIG. 2, in order to establish an attracting force on the retinal layer 13 to reposition it in controlled manner against the back wall 15 of the eye. The electrode structure 21 includes an outer cannula 23 which is curved near the distal end 25 thereof at approximately the curvature of the rear wall of the eye. The distal end of the cannula 23 includes an orifice 26 through which one or other configurations of resilient and flexible electrodes 28 may be deployed and retrieved under control of an operating physician. At the proximal end of the cannula 23, a handle 29 of convenient shape is attached to the cannula 23, and includes a finger-actuated switching mechanism 27 to manipulate the electrical signals applied to the electrodes in order to control the force applied to the retinal layer 13. A knob 31 is attached to the resilient and flexible electrodes 28 along the length of the cannula 23 and protrudes from the proximal end of the handle 29 to provide a convenient manual control mechanism for deploying and retrieving the electrodes 28. Power and control connections 33 to the electrodes 28 may extend from the outer end of the knob 31 for convenient connection to a controllable power supply 35.

In operation, the curved distal end of the cannula 23 is inserted beneath the eyelid and along the back wall of the eye to a position adjacent the location of the retinal detachment. There, the electrodes 28 are deployed through the orifice 26 at the end of the cannula 23 into position lying within a substantially spherically-curved area adjacent a selected area on the back of the eye. This may be accomplished with the aid of the knob 31 which may be pushed from an initial position remote from the outer end of the handle 29 to a position adjacent the handle, as shown, to thereby extend the electrodes 28 out of the orifice 26 at the remote end of the cannula 23. The electrodes 28 thus deployed and positioned adjacent the retinal detachment may now be energized to create an electric field for attracting the retina 13 against the back wall of the eye. There, laser photocoagulation or cryopexy or diathermy may be used in conventional manner to form scarified sites of attachment of the retina 13 to the back wall of the eye. The cannula 23 and deployed electrodes 28 may be moved rearwardly and forwardly and side to side along the back of the eye as the electrostatic force created by the energized electrodes attracts the retina 13 toward the electrodes, and in this manner effectively 'sweep' the retina 13 into position against the back wall of the eye. In addition, the operating physician may manipulate the finger control 27 in order to control the zones of energized electrodes to thereby manipulate the orientation of the attractive force upon the retina as the 'sweeping' movement of the electrodes proceeds from a region adjacent remaining attachment of the retina to the back wall of the eye toward the region of maximum detachment, from several directions. In this way, the retina 13 can be carefully repositioned against the back wall by selected combinations of movement of the electrodes about the back of the eye, and energization of selected zones of the electrodes in response to manual manipulation of the finger control 27.

Figure 3:
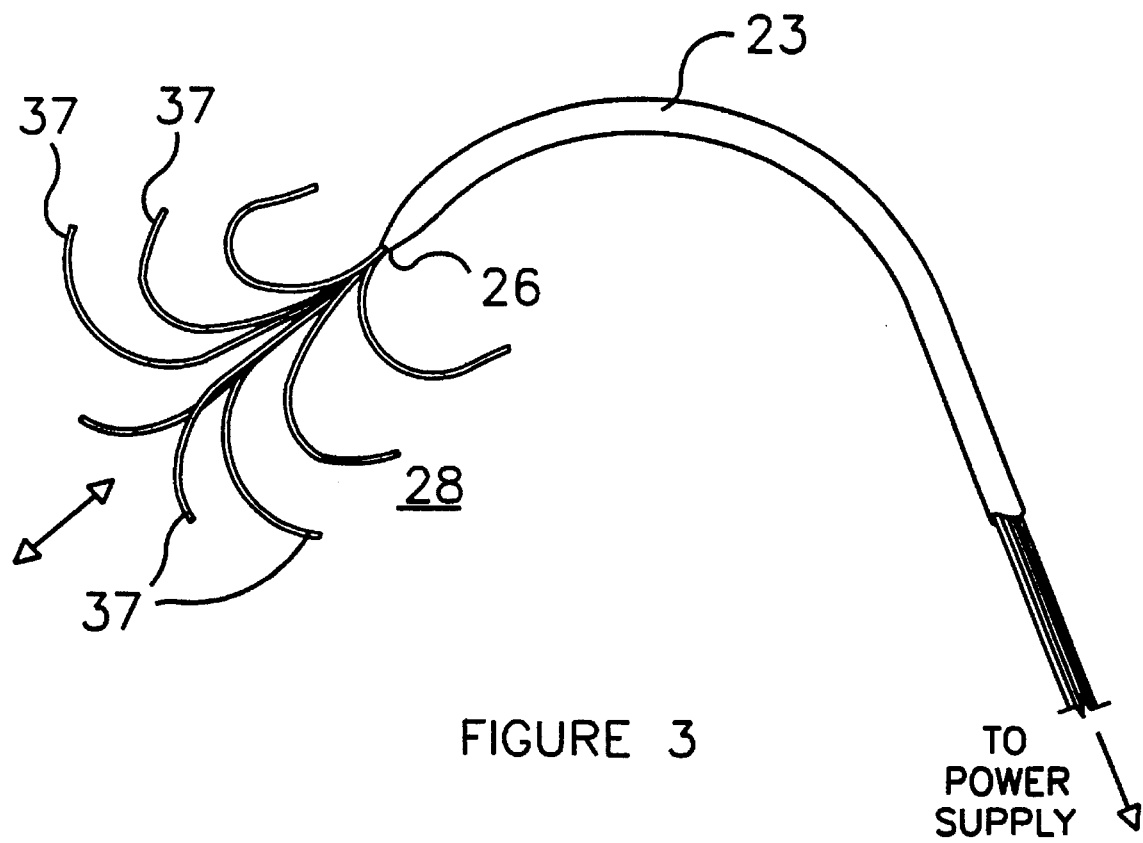
FIG. 3 is a partially cut-away illustration of one configuration of electrodes for imposing controllable repositioning force upon a detached retina according to the present invention.

Referring now to FIG. 3, there is shown one embodiment of the electrodes 28 in the form of resilient and flexible insulated conductors 37 that exhibit a latent shape when deployed through the orifice 26 at the distal end of the cannula 23. In this embodiment of the present invention, the conductors 37 are individually insulated and retained within the cannula to spread out within a selected substantially spherically curved area when extended from the orifice 26, which area then conveniently lays substantially spherically against the curvature of the back of the eye. Thus, by pushing the knob 31 that is attached to the conductors 37 along the cannula 23 from an initial position remote from the end of the handle 29, toward the position adjacent the end of the handle 29, as shown in FIG. 2, the conductors 37 extend out of the orifice 26 and unfurl according to pre-formed shapes lying substantially in a spherical area adjacent the back of the eye. These conductors 37 may be energized in several patterned combinations, including left set, or right set, or distal set, or an entire set of all electrodes combined in order to provide a 'sweep'-oriented, dynamically-controllable field suitable for controllably repositioning the retina against the back of the eye.

In operation, the electrodes 28 may include fine spring wires that are individually insulated and bundled into the cannula 23 to form a composite structure that is not greater than about 4 mm in diameter and that can be controllably deployed over an area typically of about 2 to 3 square centimeters. The conductors 37 deploy in curvilinear fashion from the orifice 26 under the manual control of the operating physician using the knob 31 to push out the conductors 37, and thereafter to retrieve the conductors 37 back into the cannula 23 by pulling the knob 31 in the direction away from the end of the handle 29. Of course, the cannula may have a generally oval-shaped cross section in order to accommodate substantial numbers of individual electrodes therethrough. Each of the conductors 37 may be coated with a biologically inert, flexible electrical insulating material such as Mylar (commercially available from DuPont Company), or polyvinyl fluoride, or polyethylene terephthalate, or other substantially biologically inert, high quality electrical insulating material that exhibits high dielectric strength against electrostatic rupture and breakdown in thin layers. The insulation material and the thickness thereof must be capable of withstanding electrical potentials of up to a few thousand volts (typically with about 0.5 mm thickness of insulation). These electrically insulated conductors are bundled or otherwise confined to move axially within the length of the cannula 23 for deployment and retrieval of the outer ends, in the manner described, under the control of the operating physician.

Figure 4:
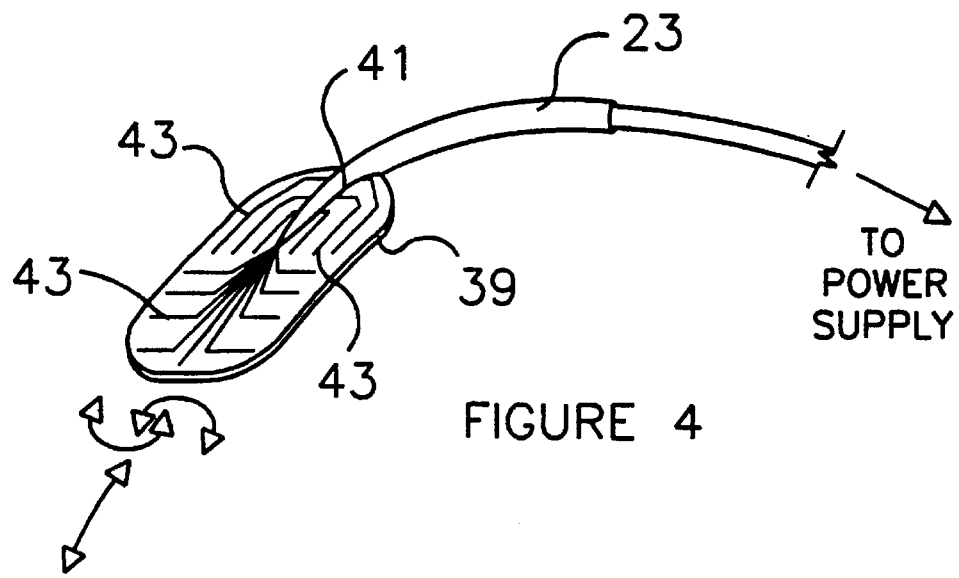
FIG. 4 is a partially cut-away illustration of another configuration of electrodes for imposing controllable repositioning force upon a detached retina according to the present invention.

Referring now to FIG. 4, there is shown another embodiment of the present invention in which the electrodes 28 are formed in a thin, flexible circuit card 39 that includes the conductors in regional sets (i.e., left set, right set, and distal set) and that can be rolled and unfurled through a slotted orifice 41 at the end of the cannula 23. Specifically, this circuit card may be formed of a flexible, biologically-inert material such as previously described on which conductors 43 are deposited or embedded or encapsulated in conventional manner to provide electrical insulation against breakdown on potentials in the range of about 1000 to 4000 volts. Such circuit card 39 can thus be formed to extend the length of the cannula 23 and be rolled therewithin along the length to the knob 31 at the outer end of the handle 29. Knob 31 can be manually manipulated to push out and unfurl the circuit card 39 through the slotted orifice 41 by pushing the knob 31 from an extended position toward the position illustrated, and by rotating the knob 31 to extend the circuit card 39 laterally through the slotted orifice 41. Once deployed to selected position on the back of the eye, the operating physician can then manipulate the finger control 27 to energize selected sets of conductors, and can also manipulate the positioning of the circuit card 39 side to side and rearwardly and forwardly in order to 'sweep' the adjacent portion of the detached retina into position against the back of the eye. Higher attractive forces can be exerted on the retina 13 using the higher range of voltages applied to the conductors, but such conductors must be insulated with dielectric material of possibly thicker dimension to assure against undesirable voltage breakdown.

Figure 5:
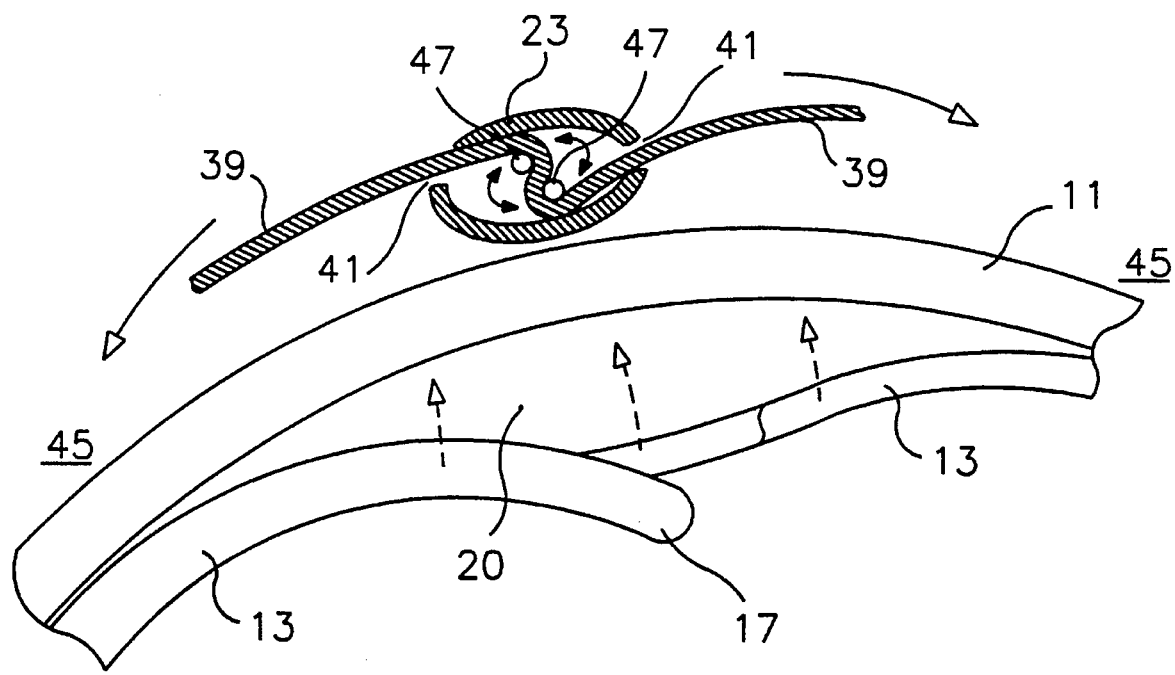
FIG. 5 is a partial sectional view of an eye with cannula and electrode structure positioned on the back wall of the eye adjacent the retinal detachment according to the present invention for controlling the deployment and retrieval of the electrode structure.

Referring now to FIG. 5, there is shown a partial, sectional view of a cannula 23 with the circuit card 39 of conductors 43 being deployed toward its final substantially spherical shape through the slotted orifice 41 at the end of the cannula 23 via rotation of the circuit card 39 and via extension of the circuit card 39 in axial direction. Supplemental stiffeners such as spring wires 47 may be incorporated into the rolled circuit card 39 in order to facilitate pushing, unfurling and rolling of the circuit card via the remotely located knob 31. The cannula and electrodes may then be moved toward a region 45 at the back side of the eye adjacent where the retina 13 remains attached to the back wall of the eye. There, the conductors 45 are selectively energized to establish an attractive force on the retina 13. This may be accomplished by energizing, say, the right set of three or four conductors with a high D.C. voltage of alternate polarities on adjacent conductors, as later described in specific detail. Alternatively, the distal set of conductors disposed closest to the outermost end of the circuit card 39 may be energized with a high D.C. voltage of alternate polarity on adjacent conductors. It is believed that this produces an electrostatic force on the retinal layer 13, which typically exhibits poor electrical conductivity, according to Coulomb's Inverse Square Law, in the manner as previously described. The adjacent conductors 43 of opposite polarity disposed on one side of the retinal layer 23 establishes a concentration of charges of corresponding polarity on the insulation layer in the region thereof disposed over each of the conductors which induces a concentration of charges of opposite polarities, perhaps from two sources, in corresponding regions of the retinal layer 23. One source is believed to be the free charges which are present in and around the environment of the retina 23, and the other source is believed to comprise the bound charge concentration associated with the polar characteristics of the retinal tissue. Accordingly, the concentrations of charges of opposite polarities at the conductors on the back of the eye and in aligned adjacent regions of the retina establish an attractive force that is a function of the magnitudes of the electrical charges on the attracted surfaces, the distances between the charged surfaces, and the dielectric constant of the electrically non-conductive material separating the charged surfaces, all as previously describe herein. The retina 13 is therefore attracted toward the back of the eye with a force that is greatest near the region 45 where the spacing between the retinal layer 13 and the conductors 43 is minimal, and is less in regions of maximum detachment of the retina from the back wall of the eye. Accordingly, the retinal layer 23 may be 'swept' into position progressively from near the adhered regions toward the detached regions of maximal spacing from the back wall of the eye using a combination of physical location of the electrical conductors 43 and magnitude of applied electrical potential. The operating physician can therefore gently reposition the retinal layer 23 against the back wall of the eye while progressively squeezing out any volume of vitreous material 19 that occupies the space 20 between the retina 13 and the back wall of the eye as the retinal layer 23 is urged against the back wall.

Figure 6:
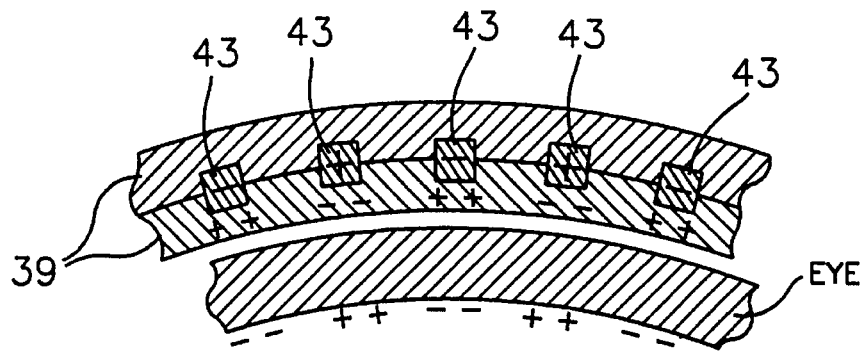
FIG. 6 is a sectional view of one embodiment of an electrode structure according to the present invention.

Referring now to FIG. 6, there is shown a sectional view of one embodiment of an electrode structure according to the present invention in which adjacent conductors or electrodes 43 are disposed between upper and lower layers 39 of insulation that forms the structure for positioning adjacent the back of the eye. The electrodes 43 are connected in alternate succession to high voltage supplies of opposite polarity so that alternate positive and negative polarities appear on adjacent successive electrodes in the structure. These electrodes 43 may be sputter coated or etch formed in conventional manner on the insulating layers 39 to form a structure substantially as illustrated in FIGS. 2 and 4 for positioning adjacent the back wall of the eye.

Figure 7:
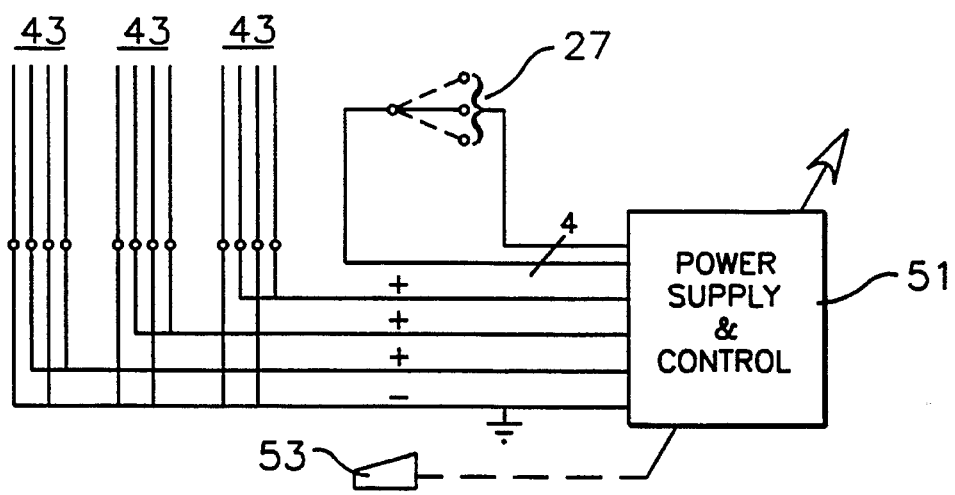
FIG. 7 is a partial schematic diagram of a power supply circuit for controlling the voltage applied to the electrode structure of the present invention.

Specifically, as illustrated in FIG. 7, there is shown a simplified schematic diagram of the connections of the electrodes associated with left, right, and distal regions or zones of the structure for selective activation in response to manual manipulation of the control switch 27. In this embodiment, the alternate electrodes are selectively connected to a high positive voltage relative to a high negative voltage or ground potential to establish an intense electrostatic field adjacent the back wall of the eye. This produces an accumulation of electrical charges on the surface of the insulating layer 39 that are attracted to the respective ones of the high static potentials or voltages on the adjacent electrodes 43, and this in turn attracts surface charges of opposite polarities in adjacent regions of the remote retinal layer 13. Ideally, the isolated regions of electrostatic charges thus formed on the surface of the insulating layer 39 are opposite the polarity of the high voltage on an adjacent electrode 43, and this charge on the surface of the insulating layer 39 attracts charges of opposite polarity in corresponding adjacent regions of the retinal layer 13 to thereby establish the attractive force between the retina 13 and the electrode structure. It is believed, however, that where conductive connections are established between the insulating layer and the layers of tissue on the back of the eye, such poorly conductive (perhaps semiconductive) composite structures may therefore establish a composite insulating structure (of composite dielectric coefficient) which is capable of supporting charge differential thereacross that thereby produces attractive force on the retina 13. The power supply may be a conventional high voltage supply that is capable of selectively applying high DC voltage to the set of electrodes 43 relative to a negative or reference potential under the control of the manual control switch 27 that is conveniently disposed on the cannula 23 and attached handle 29. This switch 27 may operate at low voltage to control to which one or more of the banks of electrodes 43 the high voltage will be applied. Conventional digital polling schemes may be used on a 4-wire connection to the control switch 27 to determine which of three or other multiple operating positions the switch is operating in. Additionally, a foot pedal controller 53 may be connected in conventional manner to control the amplitude of the high voltage supplied to the electrodes 43 under manual control of the operating physician.

Figure 8:
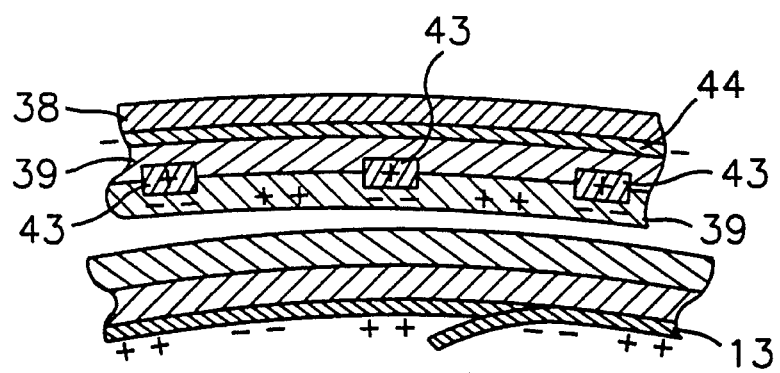
FIG. 8 is a partial sectional view of another embodiment of an electrode structure positioned adjacent the back wall of an eye according to the present invention.

Referring now to FIG. 8, there is shown a partial cross sectional view of another embodiment of the electrode structure of the present invention in which a common electrode 44 or ground plane is disposed behind the electrodes 43 that are more widely displaced to permit surface charges to accumulate in alternate array on the surface of the structure to thereby attract corresponding charged regions in the remote retinal layer 13.

It should be recognized that the apparatus and method of the present invention as described above may also be useful in attracting and otherwise positioning particles or flakes of foreign matter that penetrate the eye in order to facilitate convenient removal from a selected operational site. In addition, it should be recognized that other organs of the body than the eye may benefit from the use of the apparatus and surgical procedures described herein, for example, to control the position of particles or flakes or layers of foreign matter or tissue for more convenient surgical procedures to remove or repair the foreign matter or layer of tissue involved.

Therefore, the improved apparatus and system and method of performing retinal repairs according to the present invention uses a controllable electrostatic force imposed on the detached region of the retina in order to urge the retina into position against the back wall of the eye where it can be reattached using conventional surgical procedures such as cryopexy or diathermy or photocoagulation techniques.

What is claimed is:

1. A surgical method for selectively exerting electrostatic force at a location near the back of an eye in response to electrical signals applied to an array of plural electrodes having a layer of electrical insulation disposed thereon, the method comprising the steps of:

introducing the array of the plural electrodes to a position adjacent an area on the back of the eye and in close proximity thereto; and selectively applying electrical signals to at least a pair of the plural electrodes in the array to produce electrostatic force in said area in a direction toward the array of electrodes.

2. The method according to claim 1 in which a hollow cannula includes the plural electrodes therein near a distal end of the cannula, and the step of introducing includes positioning the distal end of the cannula at a selected location adjacent said area on the back of the eye; and deploying the electrodes from the distal end of the cannula over a selected portion of said area near the back of the eye larger than the distal end of the cannula.

3. The method according to claim 2 in which the distal end of the cannula includes an elongated slot near the distal end, and the array of electrodes includes electrical conductors disposed on a flexible circuit card with flexible electrical insulation disposed over the conductors to inhibit electrical conduction from the conductors to adjacent tissue, the method comprising:

in the step of deploying, substantially enclosing the circuit card of electrodes and insulation within the distal end of the cannula; and selectively extending and retrieving the circuit card through the elongated slot near the distal end of the cannula.

4. The method according to claim 2 in which the array of electrodes includes plural electrical conductors disposed on a flexible circuit card with flexible electrical insulation disposed over the conductors to inhibit electrical conduction from the conductors to adjacent tissue, the method comprising the steps of:

deploying the circuit card near the back of the eye over an area larger than the distal end of the cannula; and selectively energizing pairs of the plural electrodes at different locations on the circuit card to alter said select portion of the area which exhibits electrostatic force.

5. The method according to claim 1 for positioning a detached retina comprising the steps of:

selectively applying the electrostatic force to attract a region of the detached retina toward the back of the eye; and scarifying attachment of the region of the retina attracted by electrostatic force to the back of the eye.

6. The method according to claim 5 comprising the step of:

selectively altering the plural electrodes to which electrical signal is applied for selectively moving the location in said area on the back of the eye at which electrostatic force is exhibited without substantially moving the array relative to said area.

7. The method according to claim 5 wherein the step of:

selectively applying the electrostatic force includes altering the magnitude of electrical signal applied to a pair of the plural electrodes for selectively altering the electrostatic force without substantially moving the array of electrodes relative to said area.

\* \* \* \* \*